United States Patent
Tiano

[11] Patent Number: 6,065,833
[45] Date of Patent: May 23, 2000

[54] SPORTING EYEGLASSES

[76] Inventor: Sam C. Tiano, 137 Helen St., Washington, Pa. 15301

[21] Appl. No.: 09/206,386

[22] Filed: Nov. 17, 1998

[51] Int. Cl.⁷ .................................................. G02C 11/08
[52] U.S. Cl. .................................... 351/62; 351/44; 2/435
[58] Field of Search ................. 351/41, 158, 44; 2/426, 427, 428, 429, 435

[56] References Cited

U.S. PATENT DOCUMENTS

| | | | |
|---|---|---|---|
| D. 331,765 | 12/1992 | Canavan et al. | D16/112 |
| D. 380,227 | 6/1997 | Bolle | D16/314 |
| 2,027,037 | 1/1936 | Gottlieb | 88/41 |
| 3,298,031 | 1/1967 | Morgan | 2/247 |
| 3,497,294 | 2/1970 | Volk | 351/41 |
| 4,150,443 | 4/1979 | McNeilly | 2/436 |
| 4,240,718 | 12/1980 | Wichers | 351/62 |
| 5,239,320 | 8/1993 | Allendorf et al. | 351/62 |
| 5,576,775 | 11/1996 | Bolle | 351/62 |
| 5,610,668 | 3/1997 | Mage | 351/62 |
| 5,638,145 | 6/1997 | Jannard et al. | 351/62 |

*Primary Examiner*—Hung Xuan Dang
*Attorney, Agent, or Firm*—John D. Gugliotta

[57] ABSTRACT

Disclosed are sportsman's eye wear designed to overcome the difficulties and problems associated with conventional eye wear designs. The sporting eyeglasses are specially designed to afford the serious hunter, fisherman or outdoorsman superior eye protection in a stylish manner while providing a effective means by which to secure them to the user's head and maintain their position. The eyeglasses also include anti-fogging ventilation, a camouflaging veil and allow for the incorporation of prescription lenses.

7 Claims, 3 Drawing Sheets

SPORTING EYEGLASSES

BACKGROUND OF THE INVENTION

1. Field of the Invention

The present invention relates generally to eyewear, and more specifically to eyeglasses specially designed for hunting, fishing and other similar outdoor activities.

2. Description of the Related Art

Hunters, fishermen and other sportsmen face a variety of obstacles while pursuing their hobbies that mandate the use of a variety of protective devices. Among the dangers they face, eye injuries are a quite common occurrence. As a result, protective eye wear is often used to shield the user from the injuries associated with these activities. However, for the most part these devices, usually in the form of sunglasses, are large, bulky and lack the styling that is desired by many of today's outdoorsmen. While they do provide shading, polarization and ultraviolet light protection, several problems exist that make their use somewhat impractical. The eyeglasses often are not secured to the wearer to a degree sufficient to maintain their position on the wearer's head during the rigors of outdoor use. The glasses often fog up during use in damp, low-lying areas, during the early morning and evening hours when dew and fog are prevalent as well as in cold or humid environments. The glasses often draw attention to the wearer, defeating any camouflaging in a hunting scenario. Finally, prescription lenses are often not available in eyeglasses specifically designed for hunting and fishing purposes. Accordingly there is a need for a means by which hunters, fishermen and other outdoor sporting enthusiasts can acquire protective eye wear that affords them the protective features of conventional models while overcoming the drawbacks associated with the use thereof. The development of the present invention fulfills this need.

A search of the prior art did not disclose any patents that read directly on the claims of the instant invention. However, several references to ventilated and antifogging eye wear designs were discovered. These devices neither anticipate nor disclose any embodiment that would preclude the novelty and utilitarian functionality of the features of the present invention.

The following patents describe the function and design of fog-resistant sunglasses, eyeglasses, or sports goggles with means for ventilation:

U.S. Pat. No. 5,638,145 issued in the name of Jannard et al.;
U.S. Pat. No. 5,610,668 issued in the name of Mage;
U.S. Pat. No. 5,576,775 issued in the name of Bolle;
U.S. Pat. No. 5,239,320 issued in the name of Allendorf et al.;
U.S. Pat. No. 4,240,718 issued in the name of Wichers;
U.S. Pat. No. 4,150,443 issued in the name of McNielly;
U.S. Pat. No. 3,497,294 issued in the name of Yolk;
U.S. Pat. No. 2,027,037 issued in the name of Gottlieb;
U.S. Pat. No. D 380,227 issued in the name of Bolle; and
U.S. Pat. No. D 331,765 issued in the name of Canavan et al.

All of the above listed patents, with the exception of the '443 patent issued to McNielly, disclose eye wear that incorporate the use of ventilation apertures that allow air to flow there through, eliminating the accumulation of water vapor on the eye wear lenses. The McNielly disclosure discloses the incorporation of a small electric fan in conjunction with ventilation apertures that facilitate a more efficient anti-fogging means. While several features exhibited within these references may be incorporated into this invention, alone and in combination with other elements, the present invention is sufficiently different so as to make it distinguishable over the prior art.

SUMMARY OF THE INVENTION

The present invention consists of sportsman's eye wear designed to overcome the difficulties and problems associated with conventional eye wear designs. The sporting eyeglasses are specially designed to afford the serious hunter, fisherman or outdoorsman superior eye protection in a stylish manner while providing a effective means by which to secure them to the user's head and maintain their position. The eyeglasses also include anti-fogging ventilation, a camouflaging veil and allow for the incorporation of prescription lenses. The frames are constructed of a durable plastic in a wrap around design that molds around the wearer's head, secured in place with an adjustable elastic strap and forming a tight seal with the skin that prevents foreign particles from entering. A series of vents allow the eyes and skin to breathe, reducing the amount of perspiration beneath the glasses and reducing the ill-effects of fogging. The puncture-resistant lenses, available in both prescription and non-prescription form, are polarized to reduce glare and have a special ultraviolet filtering coating to protect the eyes from the sun's harmful effects. For hunters, a special camouflaging veil is available. Attached to the bottom of the eyeglass frame, the veil drapes down over the wearer's face, helping the hunter to blend in with his surroundings. Available in a variety of frame colors and lense shades, the present invention will afford the serious hunter or fisherman superior eye protection in an attractive manner.

It is therefore an object of the present invention to provide sportsman's eyeglasses that will provide adequate protection from dirt, debris and projectiles.

It is another object of the present invention to provide sportsman's eyeglasses incorporating lenses that are polarized for clear viewing.

It is another object of the present invention to provide sportsman's eyeglasses incorporating lenses that provide eye protection by filtering ultraviolet light, preventing it from reaching the wearer's eyes.

It is another object of the present invention to provide sportsman's eyeglasses that allow for use with corrective lenses.

It is another object of the present invention to provide sportsman's eyeglasses that incorporate a strong, durable frame having a wrap-around design that is tight fitting with the wearer's head, preventing dust and dirt from entering therein.

It is another object of the present invention to provide sportsman's eyeglasses that incorporate an adjustable elastic securing strap that creates a snug, secure eyeglass fit that will remain stable, even during the rigors of outdoor use.

It is another object of the present invention to provide sportsman's eyeglasses that incorporate the use of anti-fogging vents that prevent water vapor from condensing and accumulating on the eyeglass lenses.

Finally, it is an object of the present invention to provide sportsman's eyeglasses that include a detachable camouflage veil that can be used to allow a hunter to blend in with his or her surroundings.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

LIST OF REFERENCE NUMBERS

Figure 1:
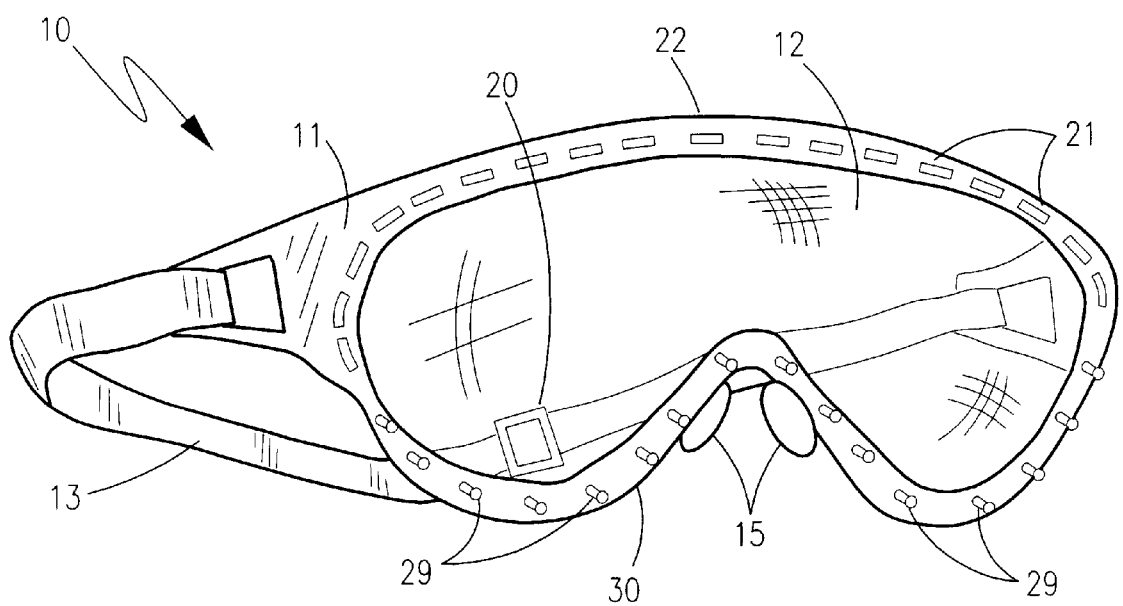
FIG. 1 is a perspective view of the sportsman's eyeglasses, according to the preferred embodiment of the present invention.
Figure 2:
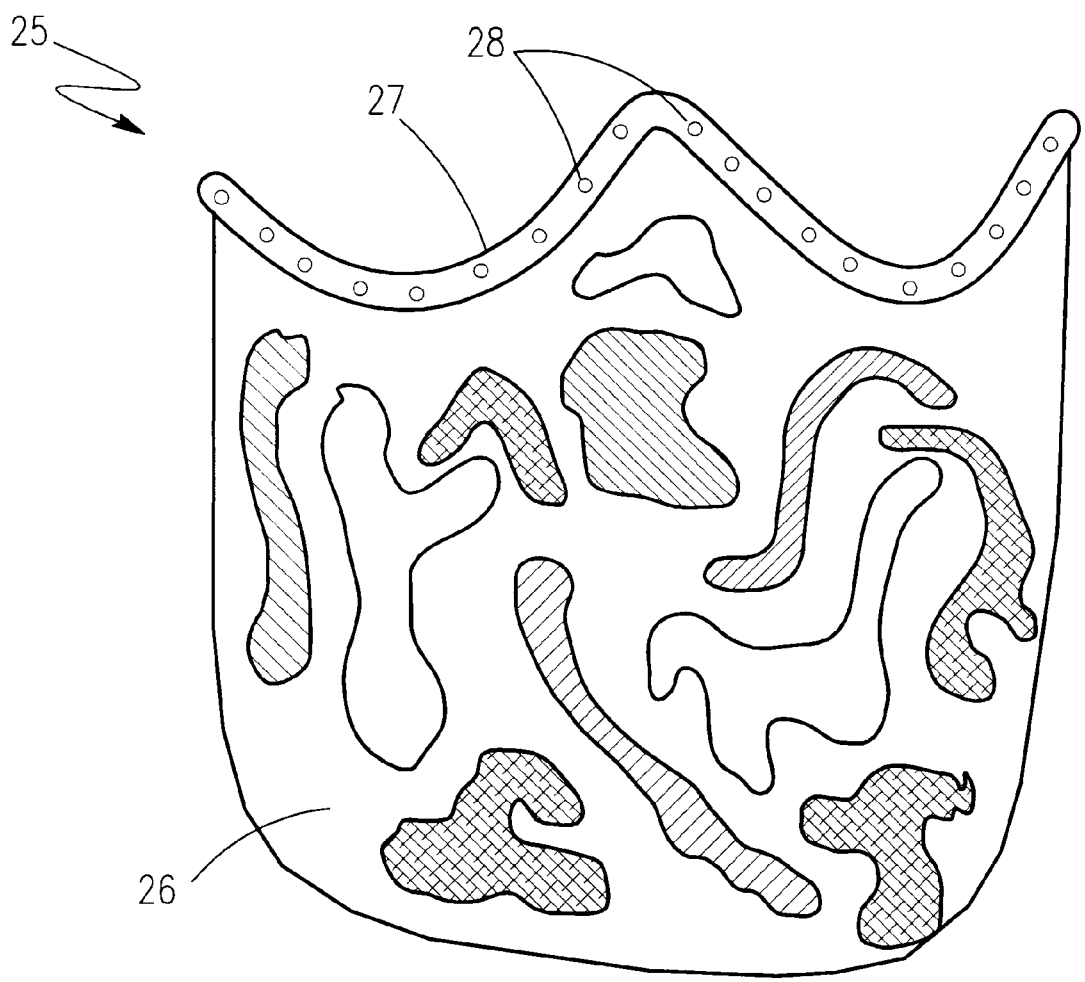
FIG. 2 is a perspective view of the camouflage veil for use in conjunction with the sportsman's eyeglasses, according to the preferred embodiment of the present invention.
Figure 3:
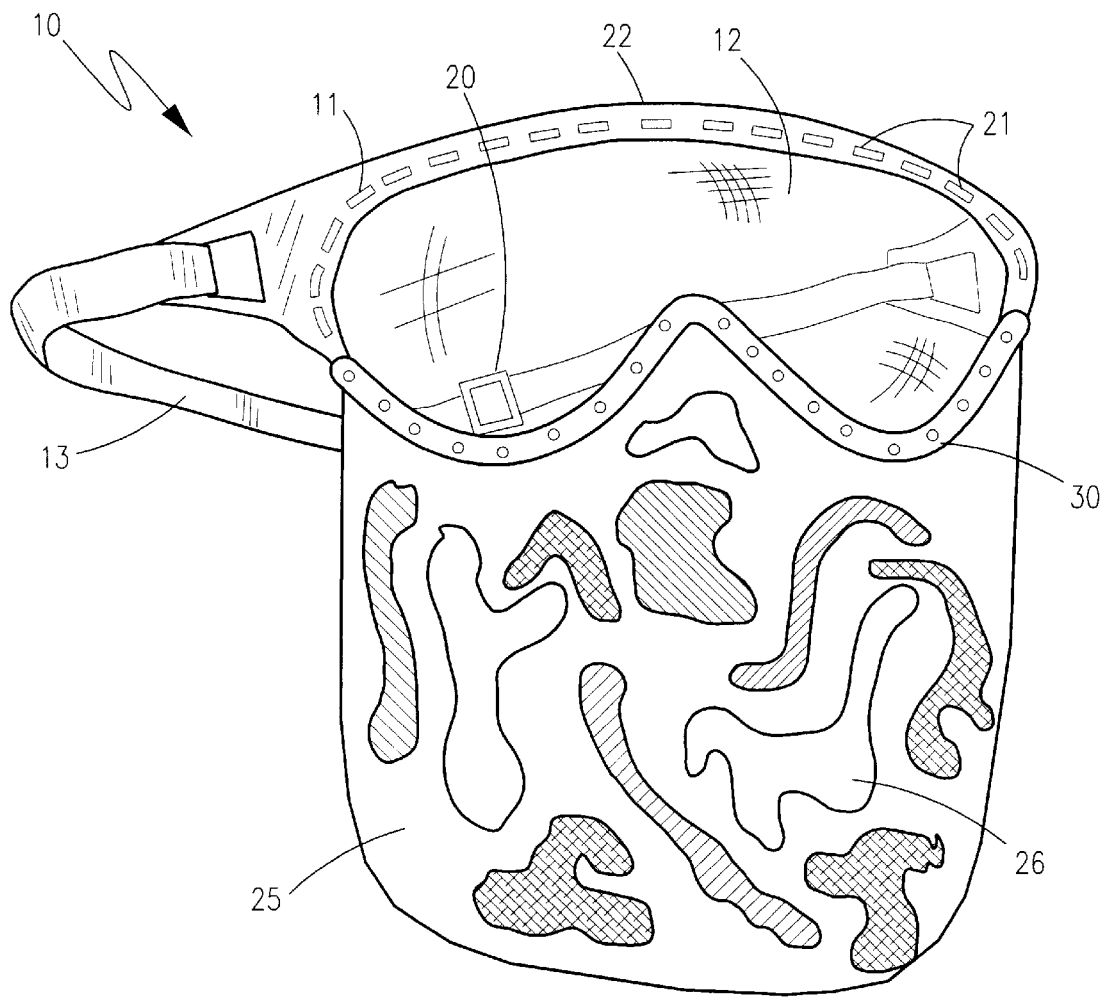
FIG. 3 is a perspective view of the sportsman's eyeglasses fit with the camouflage veil, according to the preferred embodiment of the present invention.

10 Eyeglasses 10
11 Frame 11
12 Lense 12
13 Securing Strap 13
15 Nose Rests 15
20 Sliding Buckle 20
21 Ventilation Apertures 21
22 Upper Edge 22
25 Camouflage Veil 25
26 Camouflage Material 26
27 Veil Frame 27
28 Veil Securing Apertures 28
29 Veil Securing Posts 29
30 LowerEdge 30

DESCRIPTION OF THE PREFERRED EMBODIMENTS

1. Detailed Description of the Figures

Referring now to Figures, depicted are the sportsman's eyeglasses, hereinafter eyeglasses 10, according to the preferred embodiment of the present invention. The eyeglasses 10 consist of a frame 11 that supports a lense 12 and a securing strap 13. The frame 11 is of a molded plastic construction, preferably a polycarbonate resin or other suitable material of like strength and durability, and is molded to match the contour of the wearer's (not shown) head and face, providing a tight fit therewith. The tight fit between the frame 11 and the wearer's face serves to prevent dirt, dust, debris and perspiration from entering from the sides, top or bottom and injuring or otherwise irritating the wearer's eyes. A pair of nose rests 15 support the eyeglasses 10 from the wearer's nose, preventing them from sliding up or down during use.

The securing strap 13 is constructed of an elastic material and includes a sliding buckle 20 that allows for adjusting its length. The adjustable nature of the securing strap 13 allows the user to create a custom fit in which the eyeglasses 10 fit snug against the user's face. In doing so, it is realized that the combination of and perspiration between the user's face and the eyeglasses 10 could cause the formation of condensation on the lense 12 that may impair visibility. As a result, the frame 11 includes a series of ventilation apertures 21 located along its upper edge 22 that allow for air flow freely between the eyeglasses 10 and the user's face, in order to prevent the formation of condensation.

Hunters are often faced with situations that require them to blend in with their surroundings. A camouflage veil 25, when attached to the eyeglasses 10, covers the user's face with a camouflage material 26 similar to that used to construct conventional hunting garments. The camouflage material 26 is supported by a veil frame 27 constructed of a material similar in nature to that of the frame 11 and is formed so as to coincide with the shape of the lower edge of the frame 11. The veil frame 27 includes a series of veil securing apertures 28 that coincide both in size and number to a series of veil securing posts 29 located along the lower edge 30 of the frame. The camouflage veil 25 is secured to the eyeglasses 10 by inserting the veil securing posts 29 into the veil securing apertures 28. Thus, the camouflage material 26 drapes down from the eyeglasses 10, substantially covering the user's face.

2. Operation of the Preferred Embodiment

In accordance with the preferred embodiment of the present invention and as shown in the Figures, the combination of the eyeglasses 10 and the camouflage veil 25 are used in the following manner. The user first adjusts the securing strap 13 to the appropriate length using the sliding buckle 20. The length of the securing strap 13 should be such that the frame 11 of the eyeglasses 10 fits snug against the user's face so as to prevent dust, dirt and perspiration from entering there between, but not to a degree where one would experience discomfort. Properly adjusted and fitted to the user's head, the eyeglasses 10 will remain in place, even during the rigors of outdoor activity. The flow of air through the ventilation apertures 21 will prevent the accumulation of water condensation on the lense 12. In the hunting scenario wherein one desires to blend in with typical outdoor surroundings, the user simply attaches the camouflage veil 25 to the eyeglasses 10 using the combination of the veil securing apertures 28 and the veil securing posts 29. The construction of the lense 12 will shade the user's eyes from harsh sunlight, filter out ultraviolet radiation, provide light polarization and serve as a shield from dust, projectiles or other objects. In an alternate embodiment, a prescription lense will serve to correct the user's imperfect vision.

While the preferred embodiments of the invention have been shown, illustrated, and described, it will be apparent to those skilled in this field that various modifications may be made in these embodiments without departing from the spirit of the present invention. It is for this reason that the scope of the invention is set forth in and is to be limited only by the following claims.

What is claimed is:

1. Protective eyeglasses shielding a wearer's eye's during rigorous outdoor activities, said eyeglasses comprising:

a frame having a first end opposite a second end and an upper edge opposite a lower edge defining a vision aperture, said frame positioned spanning across said wearer's eyes and allowing for substantially unobstructed vision through said vision aperture, said frame formed so as to conform to and mate with the contour of said wearer's head;

a lense supported by said frame, said lense being translucent, spanning and covering said vision aperture;

an elastic securing strap attached to and spanning between said first end and said second end of said frame, said securing strap securing said frame to said wearer's head;

a series of ventilation apertures linearly disposed along said upper edge of said frame, said ventilation apertures facilitating the flow of air therethrough and preventing the formation and accumulation of condensed water vapor on said lense; and a camouflage veil removably attached to said lower edge of said frame by a veil securing means, said camouflage veil substantially covering the portion of said wearer's face positioned below said frame.

2. The eyeglasses of claim 1 wherein said securing strap is adjustable, allowing for its length to be altered in order to facilitate fitting to the size of said wearer's head.

3. The eyeglasses of claim 1 wherein said securing strap retains said frame against said wearer's head even during times of rigorous physical activity, said frame drawn against said wearer's head forming a tight seal therewith that prevents perspiration, dust, dirt and other foreign objects from passing there between.

4. The eyeglasses of claim 1 wherein said camouflage veil further comprises an article of camouflage material attached to a veil support frame, said veil support frame formed so as to mate with the shape and contour of said lower edge.

5. The eyeglasses of claim 1 wherein said veil securing means further comprises a series of veil securing posts linearly disposed along and protruding from said lower edge, and a series of veil securing apertures linearly disposed along said veil support frame and spaced so as to coincide with said veil securing posts, wherein said veil securing posts pass through said veil securing apertures, attaching said veil support frame to said lower edge and suspending said camouflage material therefrom.

6. The eyeglasses of claim 1 wherein said lense is constructed of a puncture resistant material so as to provide eye protection to said wearer from dust, projectiles or other foreign objects.

7. The eyeglasses of claim 1 wherein said lense further comprises light shading means, light polarization means, ultraviolet radiation filtration means, means for correcting imperfect vision.

* * * * *